(12) United States Patent
Oya et al.

(10) Patent No.: US 8,012,325 B2
(45) Date of Patent: Sep. 6, 2011

(54) PLURAL-CELL GAS SENSOR WITH HEATER

(75) Inventors: Seiji Oya, Aichi (JP); Mineji Nasu, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 992 days.

(21) Appl. No.: 11/478,689

(22) Filed: Jul. 3, 2006

(65) Prior Publication Data

US 2007/0000780 A1 Jan. 4, 2007

(30) Foreign Application Priority Data

Jul. 1, 2005 (JP) ................. 2005-193988

(51) Int. Cl.
*G01N 27/419* (2006.01)
(52) U.S. Cl. ........ 204/429; 204/424; 204/425; 204/426; 204/427; 204/428; 205/783.5; 205/785; 205/781; 73/23.31; 73/23.32
(58) Field of Classification Search .......... 204/424–429; 205/783.5–785, 781; 73/23.31–23.32
See application file for complete search history.

(56) References Cited

U.S. PATENT DOCUMENTS

| | | | | |
|---|---|---|---|---|
| 4,582,657 A | * | 4/1986 | Shibata et al. ............... | 264/40.6 |
| 4,755,274 A | * | 7/1988 | Mase et al. .................... | 204/427 |
| 4,798,693 A | * | 1/1989 | Mase et al. .................... | 264/44 |
| 5,174,885 A | * | 12/1992 | Hayakawa et al. ........... | 204/425 |
| 5,288,389 A | | 2/1994 | Yamada et al. | |
| 5,529,677 A | * | 6/1996 | Schneider et al. ............ | 204/425 |
| 5,685,964 A | * | 11/1997 | Watanabe et al. ............ | 204/429 |
| 6,071,393 A | | 6/2000 | Oshima et al. | |
| 6,156,176 A | | 12/2000 | Sugiyama et al. | |
| 6,224,727 B1 | * | 5/2001 | Miyata et al. ................. | 204/425 |
| 6,344,134 B1 | | 2/2002 | Yamada et al. | |
| 6,348,140 B1 | * | 2/2002 | Matsubara et al. ........... | 204/424 |
| 6,676,817 B2 | * | 1/2004 | Noda et al. .................... | 204/424 |
| 7,316,767 B2 | | 1/2008 | Tanaka | |
| 2003/0205078 A1 | | 11/2003 | Hasei et al. | |
| 2004/0040847 A1 | | 3/2004 | Suzuki | |
| 2004/0069630 A1 | | 4/2004 | Tanaka et al. | |
| 2004/0084309 A1 | | 5/2004 | Ando et al. | |

FOREIGN PATENT DOCUMENTS

| | | |
|---|---|---|
| EP | 0 930 501 A2 | 7/1999 |
| JP | 2000-266723 | 9/2000 |
| JP | 2003-75397 A | 3/2003 |
| JP | 2003-294697 A | 10/2003 |
| JP | 2004-85474 A | 3/2004 |
| JP | 2004-93307 A | 3/2004 |
| JP | 2004-157063 | 6/2004 |
| JP | 2004-294078 A | 10/2004 |

* cited by examiner

*Primary Examiner* — Keith Hendricks
*Assistant Examiner* — Bach Dinh
(74) *Attorney, Agent, or Firm* — Sughrue Mion, PLLC

(57) ABSTRACT

A plural-cell gas sensor including at least an oxygen pump cell (40) comprising a solid electrolyte ceramic layer; an internal space (210) formed between the cells; and a heater substrate (190) arranged on the side of the oxygen pump cell; the heater substrate heating the oxygen pump cell that pumps oxygen out of the internal space.

15 Claims, 3 Drawing Sheets

PLURAL-CELL GAS SENSOR WITH HEATER

BACKGROUND OF THE INVENTION

1. Field of the Invention

The present invention generally relates to a plural-cell gas sensor or rather a multi-cell gas sensor for measuring concentration of a specific gas component such as oxygen, NOx, CO, HC and $NH_3$ contained, for instance, in an exhaust gas exhausted from an automobile combustion engine and/or for controlling fuel-combustion in the engine. The present invention particularly relates to a plural-cell gas sensor including plural electrochemical cells including an oxygen pump cell and an oxygen monitor cell each comprising a solid electrolyte ceramic material; an internal space formed between the cells; and a heater for heating and activating the cells. More specifically, the present invention relates to an improved plural-cell gas sensor including at least an oxygen pump cell comprising a solid electrolyte ceramic layer; an internal space formed between the cells; and a heater substrate placed near the oxygen pump cell; the oxygen pump cell, being heated with the heater substrate and pumping out oxygen from the internal space, exhibiting improved activation.

2. Description of the Related Art

A conventional gas sensor including a plurality of solid electrolyte cells and a heater for heating the cells is disclosed, for instance, in U.S. Pat. Nos. 6,071,393, 6,344,134 and U.S. Patent Application Publication No. US-2004-0084309-A1 in which the heater is arranged in the vicinity of the gas sensor so as to activate the cells.

Conventionally, the plural-cell gas sensor includes at least one internal space formed by an oxygen pump cell and an oxygen monitor cell or an EMF cell (i.e., an electromotive force cell). An exhaust gas under measurement is introduced into the internal space through a gas-diffusion controlling aperture or inlet. The oxygen monitor cell partly constituting a wall of the internal space monitors an oxygen partial pressure in the internal space. The oxygen contained in the gas under measurement contacting an internal electrode of the oxygen pump cell that partly constitutes a wall of the internal space, dissociates into oxygen ions under a voltage applied across electrodes of the oxygen pump cell. The oxygen ions dissociated at the internal electrode of the pump cell flow through an oxygen-ion conductive solid electrolyte layer of the pump cell to an external electrode thereof. At the external electrode, the oxygen ions recombine to form oxygen that drains out to the ambient atmosphere or to the exhaust gas outside the sensor. The applied voltage is normally feedback-controlled by a monitor cell which monitors an EMF (electromotive force) corresponding to an oxygen partial pressure (or oxygen concentration) of the internal space so that the oxygen partial pressure inside the internal space is maintained at a constant low level value that is near zero. The oxygen ion current which has passed through the internal and external electrodes of the oxygen pump cell represents an oxygen concentration of the exhaust gas under measurement entering the internal space through the gas-diffusion limiting inlet. This is because the internal oxygen partial pressure is controlled to a constant low level. A residual gas in the internal space having a reduced oxygen partial pressure under an oxygen-pumping action of the pump cell may be admitted to a second internal space, wherein a specific gaseous component such as NOx, HC and CO in the residual gas is detected or analyzed by a gas detection cell partly constituting a wall of the second internal space.

Conventionally in this type of plural-cell gas sensor having an internal space formed therein, a heater has been placed in the vicinity of the sensor cells each comprising a solid electrolyte ceramic such as zirconia that becomes oxygen-ion conductive at high temperatures beyond about 300° C. However, because the oxygen pump cell is required to quickly and smoothly pump oxygen out of the internal space to the ambient gas atmosphere, an external air gap or channel for draining oxygen from the exterior electrode of the pump cell so as to vent to the ambient gas atmosphere has been formed between the external electrode of the pump cell and the heater substrate. In other words, in conventional sensors, a heater substrate has not been directly adhered to a surface of the exterior electrode of the pump cell, or otherwise. Rather, the heater substrate has been provided on a side of another, such as a monitor cell, that is not required to quickly pump out a large amount of oxygen from the internal space to the ambient atmosphere.

3. Problems to be Solved by the Invention:

However, in the type of plural-cell gas sensor that has an external air gap or channel formed between the oxygen pump cell and the heater so as to drain oxygen from the internal space to the external air gap, a heating efficiency or activating efficiency of the pump cell by the heater is not satisfactorily high enough to meet gas sensor requirements of late requiring fast activation of the sensor cells. This is because heat from the heater for activating the pump cell is thermally transferred via the external air gap formed between the pump cell and the heater substrate or via a spacer inserted between the heater substrate and a periphery of the pump cell for forming the external air gap.

In addition to such heating inefficiency caused by the heater substrate heating the oxygen pump cell, due to the external air gap formed between the pump cell external electrode and the heater substrate, the mechanical strength of the plural-cell gas sensor is comprised. Further, in co-firing a green laminate of plural cell layers laminated with a green heater substrate thereon, a careful firing process is needed to guarantee that a uniform external air gap is formed between the pump cell and the heater substrate.

In a modified conventional plural-cell gas sensor as disclosed in U.S. Patent Application Publication No. US-2004-0084309-A1, in which the heater substrate is not laminated on the side of the oxygen pump cell but rather on the side of an oxygen monitor cell, the activation of the oxygen pump cell is not satisfactory. This is because the heat from the heater substrate to the oxygen pump cell is transferred via the other cell layer, a spacer forming an internal space and via the internal space.

In addition, leakage current from the heater, superimposed on weak signals of the oxygen monitor cell or of the gas detection cell, may disadvantageously cause inaccurate gas measurements when the heater substrate is laminated on the side of the oxygen monitor cell or the gas detection cell. However, in that case, the external air gap to be formed between the oxygen pump cell and the heater substrate, which structurally weakens the plural-cell gas sensor, may be eliminated.

SUMMARY OF THE INVENTION

The present invention has been achieved so as to solve the above-mentioned problems including inefficient activation of the oxygen pump cell incorporated in a plural-cell gas sensor that is heated by a heater.

It is therefore an object of the invention to provide an improved plural-cell gas sensor including at least an oxygen pump cell and a heater for heating the pump cell, the oxygen pump cell having an improved activation when heated by the heater.

It is another object of the invention to provide a co-fired plural cell gas sensor, including a co-fired laminate of layers constituting an oxygen pump cell, an oxygen monitor cell and a heater substrate for heating the cells, the oxygen pump cell having improved activation when heated by the heater substrate, and the co-fired plural-cell gas sensor further having improved mechanical and structural strength.

The above objects of the invention are achieved by providing a plural cell gas sensor (1) including: an oxygen pump cell (40) comprising a first oxygen-ion conductive solid electrolyte ceramic layer (170) and internal and external porous electrode layers (42 and 44) sandwiching the first solid electrolyte ceramic layer (170); an oxygen monitor cell (30) comprising a second oxygen-ion conductive solid electrolyte ceramic layer (150) and inner and reference electrode layers (32 and 34) sandwiching the second oxygen-ion conductive solid electrolyte ceramic layer (150); an internal space (210) defined between the oxygen pump cell layer (40) and the oxygen monitor cell (30); a gas-diffusion inlet (214) through which a gas under measurement enters the internal space (210); a heater substrate (190) comprising insulating ceramic layers (192 and 194) and a heating resistor (60) embedded in the insulating ceramic layers (192, 194); and a thermal conductive porous ceramic layer (182) sandwiched by the oxygen pump cell (40) and the heater substrate (190); wherein the thermal conductive porous ceramic layer (182) adjoins the external porous electrode (44) of the oxygen pump cell (40) and the insulating ceramic layer (192) of the heater substrate (190) such that oxygen inside the internal space (210) is pumped out through the first oxygen ion conductive solid electrolyte layer (170) and drained off from the external porous electrode (44) of the pump cell (40) via the porous ceramic layer (182) so as to vent to an ambient gas atmosphere outside the gas sensor (1) and such that heat from the heater substrate (190) is directly transferred via the thermal conductive porous ceramic layer (182) to the external electrode (44) of the oxygen pump cell (40).

Importantly, since the thermal conductive porous ceramic layer (182) adjoining the external electrode (44) of the oxygen pump cell (40) and the insulating layer (192) of the heater substrate (190) is arranged between the external electrode (44) and the insulating layer (192), the oxygen can drain off the porous ceramic layer (182) so as to vent to the ambient gas atmosphere. Furthermore, heat from the heater substrate (190) can directly transfer through the porous ceramic layer (182) to the external porous electrode layer (44) of the oxygen pump cell (40). As a result, fast thermal transfer from the heater substrate (190) to the external porous electrode layer (44) of the oxygen pump cell (40) is advantageously attained, simultaneously assuring that oxygen can drain off from the external electrode of the pump cell via the porous ceramic layer (182) so as to vent to the ambient gas atmosphere outside the plural cell gas sensor (1). Therefore, activation of the oxygen pump cell (40) by the heater substrate (190) heating the pump cell (44) incorporated in the plural cell gas sensor (1) according to the invention, is advantageously far improved, compared to a conventional plural cell gas sensor.

In another aspect of the invention, the porous ceramic layer (182) adjoining the porous electrode layer (44) of the oxygen pump cell (40) and the insulating ceramic layer (192) of the heater substrate (190) has a porosity that is preferably greater than that of the exterior porous electrode (44). The porosity of the external porous electrode layer (44) may be preferably 1% to 25%, or more preferably 5-20%. The porosity of the thermal conductive porous ceramic layer (182) may be preferably 20% to 80%, or more preferably 30-70%. Since the porous ceramic layer (182) is more porous than the porous electrode (44) of the pump cell (40), according to this aspect of the invention, the porous ceramic layer (182) is not adversely clogged by oxygen therein so that the oxygen in the internal space (210) is smoothly pumped out and drained off from the external porous electrode layer (44) through the porous ceramic layer (182) so as to vent to the ambient gas atmosphere outside the sensor (1), under pumping action of the oxygen pump cell (40) across which a dc voltage is applied. The porosity of the porous ceramic layer (182) may be determined from a SEM (scanning electron microscope) photograph taken on a cut surface of the porous ceramic layer, in which the pore area of the SEM photograph divided by the total area of the SEM photograph is defined as the porosity.

Preferably, the porous ceramic layer (182) adjoining the external electrode (44) of the pump cell (44) and the heater substrate (190) preferably have a total thickness designed to be about 20-500 µm. The porous ceramic layer is packed into a channel or recess formed by the insulating substrate (192) of the heater substrate and a ceramic spacer (180) laminated thereto. The porosity of the porous ceramic layer (182) may be adequately designed in view of the transverse area of the channel packed with the porous layer and exposed to the ambient gas atmosphere, through which area of the channel the oxygen can transversely vent to the ambient atmosphere; and in view of the length of the channel filled with the porous layer (182).

Notably, the word "porous" or "porosity" as described herein is directed to "open pores" capable of passing oxygen molecules through the channel filled with the porous ceramic layer (182) from the external electrode (44) to the ambient gas atmosphere.

A preferable main material for the thermal conductive porous ceramic layer (182) is, for example, alumina, zirconia, mullite, spinel or a mixture thereof. A porous alumina ceramic layer is suitable as the porous ceramic layer (182) in view of having the fastest thermal transfer among these materials.

A porous ceramic layer containing alumina and/or zirconia may be more suitable as the thermal conductive porous ceramic layer (182) in the case that a co-fired plural cell gas sensor is made by co-firing a green laminate of layers constituting the oxygen pump cell, the oxygen monitor cell (30), the porous ceramic layer filled between the external electrode of the pump cell and the heater substrate, and other layers such as a spacer layer (180) and a gas detection cell layer (20). This is because the porous ceramic comprised of alumina and/or zirconia forming the porous ceramic layer (182) can mediate a difference in thermal expansion between a zirconia solid electrolyte cell layer and an insulating alumina ceramic layer, thus preventing possible cracks in an external electrode surface of the oxygen pump cell during co-firing. Especially when the porosity of the porous ceramic layer (182) is designed to be higher than but close to that of the external electrode layer (44), the mechanical strength of the plural cell gas sensor (1) is improved, compared to a conventional plural gas sensor without having a porous ceramic layer between the heater substrate and the external electrode of the oxygen pump cell. The porosity difference therebetween is preferably less than 50%, or more preferably less than 30%.

When greater mechanical and structural strength is required, the porous ceramic layer (182 or 183) sandwiched by the heater substrate (190) and the oxygen pump cell (40) may extend beyound a periphery of the external electrode (44) and be partly surrounded by the ceramic spacer (180), such that a portion of the ceramic spacer (180) is exposed to the ambient gas atmosphere for draining off oxygen from lateral sides or a distal end of the multilayer plural cell gas sensor (1 or 2).

In another aspect of the invention, the thermal conductive porous ceramic layer adjoining the external electrode (44) of the oxygen pump cell (40) and the heater substrate (190) may comprise plural porous layers (241, 243) adjoining one another, each layer being different from other layer (s) in terms of material composition or porosity.

When plural porous layers (241, 243) constitute the thermal conductive porous ceramic layer, the porosity of the porous layer (241) located closest to the heater substrate (190) is preferably lower than the other porous layer(s). Such arrangement is preferably adopted in view of thermal transfer efficiency from the heater substrate to the external electrode layer (44) of the oxygen pump cell (40), in view of connecting strength of the porous ceramic layer (182) connecting to the heater substrate (190), and in view of oxygen-permeability at the porous ceramic layer (243) closest to the external electrode (44) of the oxygen pump cell (40).

When the plural porous ceramic layers (241, 243) comprising porous alumina and porous zirconia are arranged for adjoining the heater substrate (190) and the external electrode (44) of the oxygen pump cell (40), the porous ceramic layer (243) located closest to the external electrode (44) of the oxygen pump cell (40) may preferably contain more porous zirconia than the porous layer located closest to the heater substrate (190), in view of preventing cracks from forming in the surface of the external electrode (44) while co-firing the laminate and in view of increasing connecting strength of the plural porous ceramic layers adjoining the external electrode (44).

Additionally, a gas detection cell layer (20) comprising a third zirconia oxygen-ion conductive solid electrolyte layer (130) and a gas detection electrode (22) and a reference electrode (24) formed on an inner surface of the third solid electrolyte layer (130) may be provided for detecting the concentration of a specific gas component in the gas that enters a second internal space (211) and/or a third internal space (230) through a second gas-diffusion inlet (216) connecting to the first main internal space (210). The gas in the main internal space (210), reduced in oxygen concentration due to action of the oxygen pump cell (40) and thereby made rich in a specific gaseous component concentration, diffuses into the second and/or third internal spaces (211, 230) through the second inlet (216) so as to be analyzed by the gas detection cell (20) that may be positioned in the second or third internal spaces (211, 230), more preferably positioned in the third internal space (230).

The first, second and third zirconia oxygen-ion conductive solid electrolyte layers (170, 150 and 130) constituting the oxygen pump cell (40), the oxygen monitor cell (30) and the gas detection cell (20), respectively, may preferably comprise stabilized or partially stabilized zirconia and 10-80% by weight of alumina, when the plural-cell gas sensor is made by co-firing a green (unfired) laminate comprised of a green heater substrate comprising alumina ceramic, a green oxygen-pump cell layer comprising a green zirconia solid electrolyte layer and a green porous ceramic layer sandwiched by the heater substrate and the oxygen pump cell layer. This is because alumina grains (high-purity alumina grains) dispersed in the zirconia solid electrolyte ceramic layer mediate a difference in thermal expansion between the alumina ceramic substrate and the zirconia layers so as to prevent cracking of the cell layers and the porous ceramic layer during co-firing of the laminate without adversely affecting ion-conductivity of the zirconia solid electrolyte layer of the pump cell.

The present invention has been described above, with numerical references included for explaining elements constituting the plural-cell gas sensor as illustrated in the accompanying drawings. However, the present invention should not be construed as being limited thereto.

DETAILED DESCRIPTION OF THE INVENTION

The present invention will next be described in further detail by reference to the drawings. However, the present invention should not be construed as being limited thereto.

Figure 1:
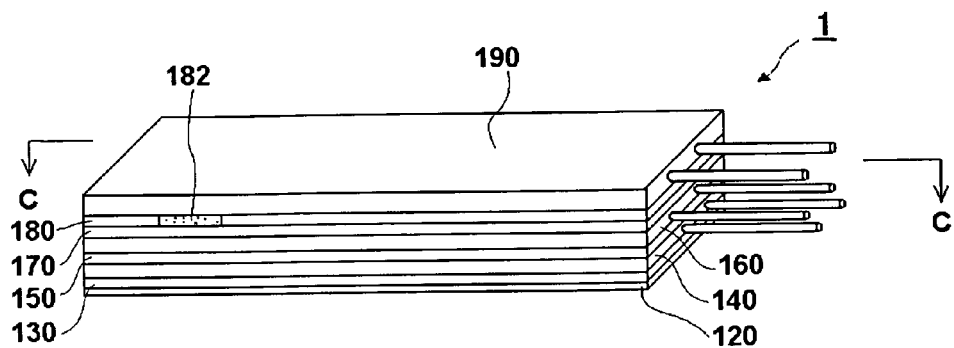
FIG. 1 is a schematic view of a plural-cell gas sensor (1), according to an embodiment of the present invention.
Figure 2:
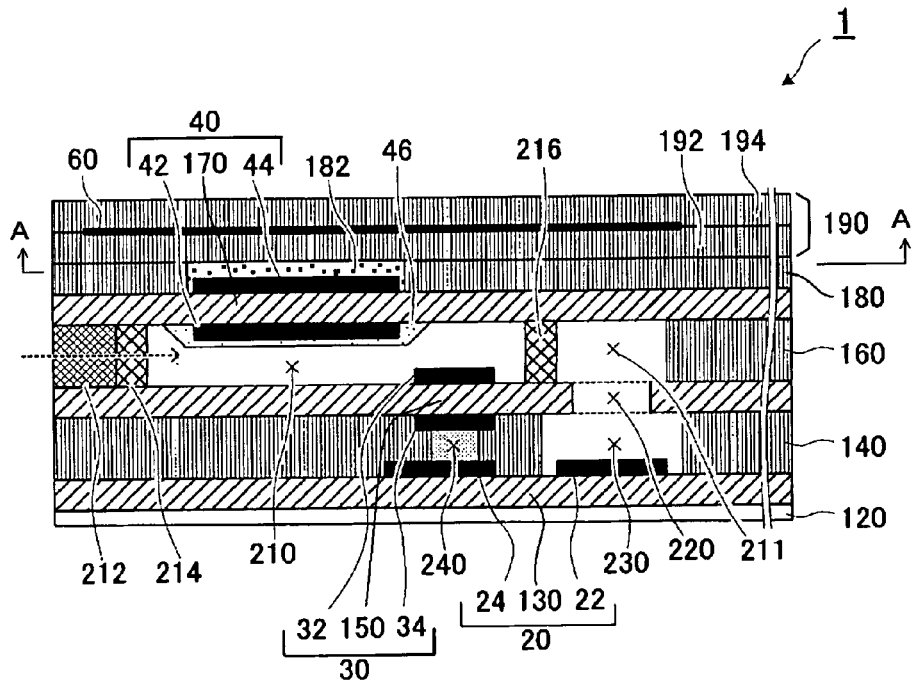
FIG. 2 is a schematic cross-sectional view, as cut along line C-C of FIG. 1, showing an internal multi-layer structure of the plural-cell gas sensor (1).
Figure 4:
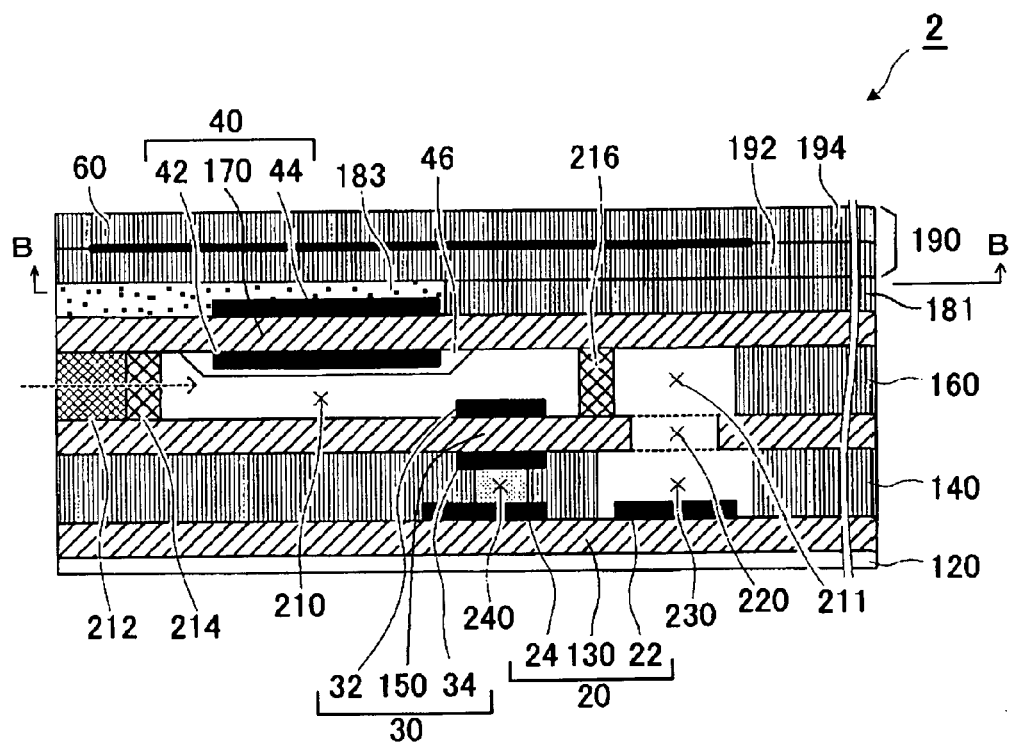
FIG. 4 is a schematic cross-sectional view, showing an internal multi-layer structure of the plural cell-gas sensor (2), according to another embodiment of the present invention.
Figure 6:
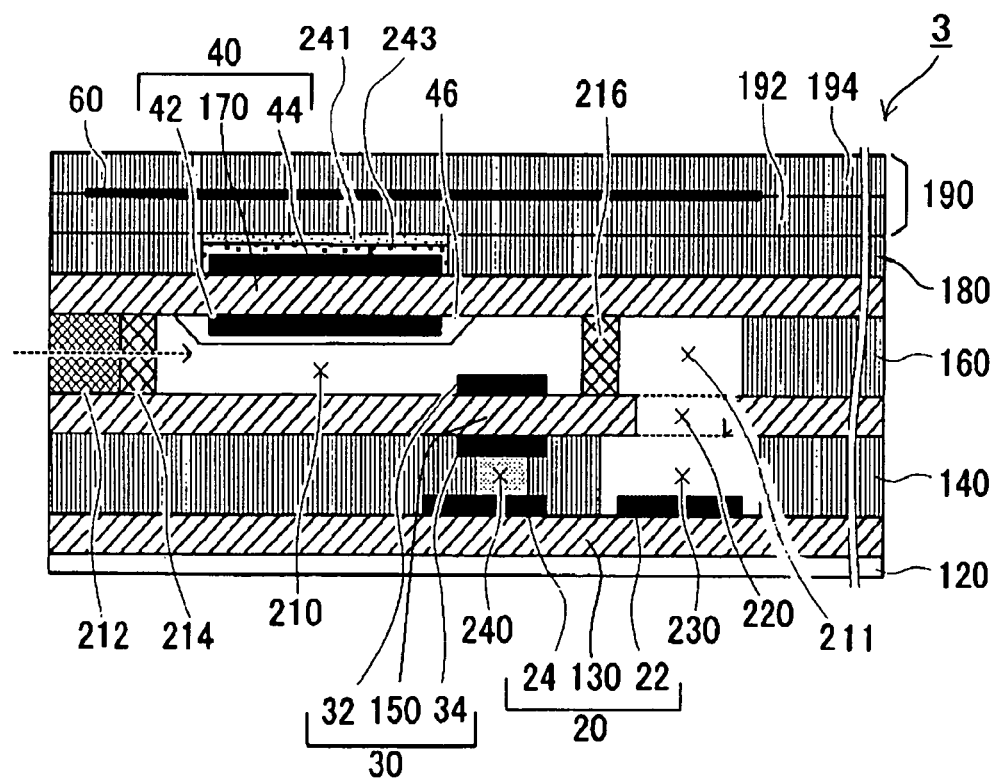
FIG. 6 is a schematic cross-sectional view, showing an internal multi-layer structure of the plural cell-gas sensor (2), according to a third embodiment of the present invention.

The present invention relates to a plural-cell gas sensor (or rather a multi-cell gas sensor) including a plurality of electrochemical cells, having a longitudinally extending rod-like appearance as shown in FIG. 1 and having a multilayer internal structure as schematically illustrated in FIG. 2, FIG. 4 and FIG. 6.

Referring to FIG. 2, the plural-cell gas sensor (1) according to an embodiment of the invention, includes an oxygen pump cell layer (40) comprising a first zirconia solid electrolyte layer (170) and internal and external porous electrodes (42 and 44) sandwiching the solid electrolyte layer (170). The porous electrodes (42 and 44) may comprise Pt (platinum) and about 1-10 weight % of zirconia, having a porosity of about 1-25%, preferably of 5-20%, most preferably of 10-15%. When the plural-cell gas sensor is designed for measuring the concentration of a specific gas component such as NOx, CO and HC contained in the gas under measurement, the inner electrode (42) may be doped with 0.1-2% by weight of Au (gold) and/or Cu (copper) to the extent that the specific gaseous component such as NOx, CO and HC contacting the inner electrode (42) does not substantially dissociate whereas oxygen does.

A main first internal space (210) is formed between the oxygen pump cell layer (40) and an oxygen monitor cell layer (30) that comprises a second zirconia solid electrolyte layer (150) and internal and external porous electrodes (32 and 34) sandwiching the second solid electrolyte layer (150). A porous protective ceramic layer (46) comprising alumina or spinel and having a thickness of about 5-50 µm may be coated on the internal porous electrode layer (42), so as to protect the inner electrode from being poisoned by Si (silicon), Pb (lead), etc., possibly included in the gas under measurement contacting the inner electrode (42).

The oxygen monitor cell monitors oxygen partial pressure inside the main first internal space (210) so as to control the gas entering the second internal space (211) communicating with a third internal space (230) via an aperture (220). This is because an EMF (electromotive force) potential produced between its internal electrode (32) formed in the main first internal space (210) and external-reference electrode (34) formed in a fourth internal space (240) in communication with a constant oxygen partial pressure referential gas, such as the air outside the plural-cell gas sensor (1) is detected, so as to be maintained at a constant low level by pumping action of the oxygen pump cell (40) across which electrodes a dc voltage is applied under feedback control of the monitor cell (30).

A first gas-diffusion inlet (214) is formed between the first and second solid electrolyte layers (170 and 150) such that a gas under measurement such as an exhaust gas exhausted from an internal combustion engine enters the first main internal space (210) only through the first gas-diffusion inlet (214). The gas-diffusion inlet (214) is joined with or packed with a gas-permeable layer (212) having a gas diffusion resistance which physically controls or limits the gas under measurement passing through the gas diffusion inlet (214) and the gas permeable layer (212) and then entering an adjacent second internal space (211) formed between the first and second solid electrolyte layers (170 and 150) longitudinally extended in the rod-like multilayer plural-cell gas sensor (1).

The second internal space (211) communicating with the first internal space (210) is defined between the first and second solid electrolyte layers (170 and 150) by an insulating ceramic spacer (160) and a second gas-diffusion inlet (216) is formed between the main internal space (210) and the second internal space (211). The second gas-diffusion inlet (216) physically controls the gas molecules entering from the main internal space (210) to the second internal space (211). The second gas-diffusion inlet (216) may be packed with a gas permeable layer having a certain gas-diffusion resistance that is lower than that of the gas permeable layer (212) joined with the first gas-diffusion inlet (214).

The plural-cell gas sensor (1) may further include a gas detection cell (20) comprising a third zirconia oxygen-ion conductive solid electrolyte layer (130) and a gas detection electrode (22) and a reference electrode (24) formed on a common inner surface of the third solid electrolyte layer (130). The detection cell (20) detects the concentration of a specific gas component in the gas that enters from the first main internal space (210) through the second gas-diffusion inlet (216) into the second internal space (211), and then enters a third internal space (230) that communicates with the second internal space (211) via an aperture (220) penetrating the second solid electrolyte layer (150).

An insulating ceramic layer (160) made of alumina ceramic intervenes between the first and second oxygen ion conductive solid electrolyte layers (170 and 150) so as to be electrochemically isolated from one another. The insulating alumina ceramic layer (160) is arranged as a spacer for forming the main first internal space (210) and the second internal space between the first and second solid electrolyte layers (170 and 150). An insulating ceramic layer (140) made of alumina ceramic intervenes between the second and third oxygen ion conductive solid electrolyte layers so as to be electrochemically isolated from one another. The insulating alumina ceramic layer (140) is arranged as a spacer for forming the third internal space (230) and a fourth internal space (240) between the second and third solid electrolyte layers (150 and 130).

The fourth internal space (240) is a common oxygen-reference chamber having a reference level oxygen concentration therein to which the external electrode (34) of the oxygen monitor cell (30) and the reference electrode (24) of the gas detection cell (20) are exposed. All the electrodes of the cells may comprise porous platinum.

The outer surface of the third oxygen ion conductive solid electrolyte layer (130), a part of which layer constitutes the gas detection cell (20), is laminated and covered with a protective insulating ceramic layer 120 made, for example, of alumina ceramic.

Figure 5:
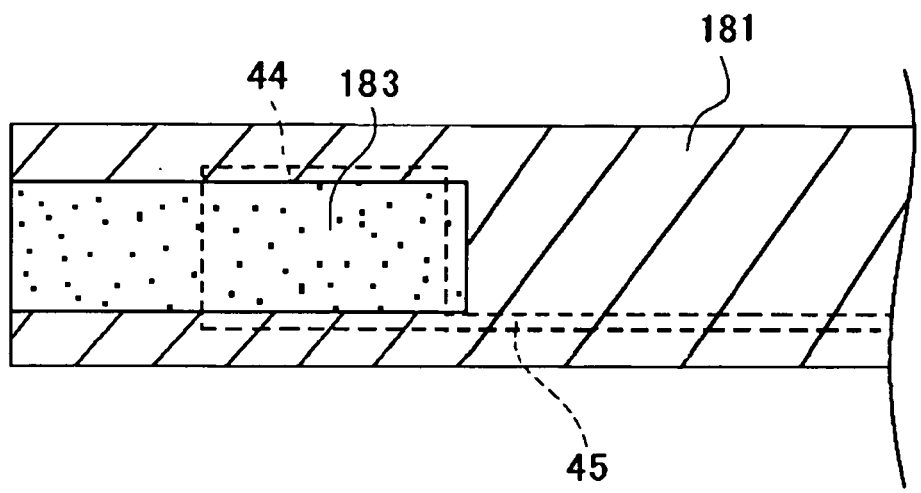
FIG. 5 is a schematic cross-sectional view, as cut along line B-B of FIG. 4, showing a porous ceramic layer (183) formed on an external electrode (44) of the oxygen pump cell (40) of FIG. 4.

On the external side of the first oxygen ion conductive solid electrolyte layer (170), a part of which layer constitutes the oxygen pump cell (40), an insulating spacer layer (180) made, for example, of alumina and/or zirconia ceramic is laminated. The insulating spacer layer (180) is laminated on a metallic wire (45) of the external electrode (44) of the oxygen pump cell (40), but not laminated on the external electrode (44) and two lateral sides thereof, as illustrated by hatched lines in FIG. 3, such that oxygen permeating through the thermal conductive porous layer (182) can drain off from the lateral sides of the plural-cell gas sensor (1). Referring to FIGS. 4 and 5 which illustrates another embodiment, an insulating spacer layer (181) is laminated on the metallic wire (45) of the external electrode (44), but not laminated on the external electrode (44) and a distal end side thereof, such that oxygen permeating the thermal conductive porous layer (183) drains off from the distal end of the plural-cell gas sensor (2). The metallic wire (45) electrically connecting with the external electrode (44) extends longitudinally through the rod-like gas sensor (1) so as to be projected or exposed at a posterior end thereof. All metallic wires for electrical connection of the cell electrodes internally extend through the plural cell gas sensor (1) to be connected with an external gas sensor control device at a posterior distal end of the rod-like gas sensor (1) having a prismatic shape, as illustrated in FIG. 1.

A heater substrate (190) comprising two insulating ceramic layers (192, 194) and a heating resistor (60) comprising a Pt fine wire embedded therein between the insulating ceramic layers (192, 194) is laminated on the insulating spacer layer (180 or 181) such that the external electrode (44) of the oxygen pump cell (40) is spaced apart from the insulating ceramic layer (192) of the heater substrate (190).

A thermal conductive porous ceramic layer (182 or 183) adjoining the external electrode (44) of the oxygen pump cell (40) and the inner insulating ceramic layer (192) of the heater substrate (190) is formed between the oxygen pump cell (40) and the heater substrate. The thermal conductive porous layer (182 or 183) is preferably formed by co-firing a green (unfired) layer thereof with a green insulating ceramic layer of the heater substrate and with a green external electrode layer (44) of the oxygen pump cell layer (40) at a temperature of about 1350-1600° C. so as to structurally and thermally connect the heater substrate (190) with the external electrode (44) after firing.

The thermal conductive porous ceramic layer (182 or 183) preferably comprises $Al_2O_3$ (alumina), in view of its high thermal conduction efficiency (or heat transfer efficiency) of the heat from the heating resistor (60) of the heater substrate to the external electrode (44) of the oxygen pump cell (40), when the adjoining ceramic layer (192) constituting the heater substrate (192) comprises a high thermal transfer material made of alumina. In addition to alumina, zirconia may be added to the thermal conductive porous layer (182, 183), so that the thermal conductive ceramic layer (182, 183) can be securely and uniformly attached on a surface of the external electrode (44) of the oxygen pump cell.

The insulating ceramic layers (192, 194) constituting the heater substrate (190), the ceramic spacer (180) and the thermal conductive porous ceramic layer (182, 183) may preferably comprise alumina and 0.01-10% by weight of inorganic binders such as MgO, $SiO_2$ and CaO. A metal ion-migration-preventing electrode may be embedded in the insulating ceramic layer (192 or 194) of the heater substrate (40) and connected to a negative polarity side of the heating resistor (60) so as to prevent harmful migration of metal ions such as Ca, Si and Mg derived from the inorganic binders to the heating resistor (60).

The thermal conductive porous ceramic layer (182, 183) may comprise a plurality of porous ceramic layers, for example, two laminated porous layers (241, 243) as shown in the plural-cell gas sensor (3) illustrated in FIG. 6, the layers being different from one another in material composition and/or porosity. The porosity of the porous ceramic layer (241) adjoining the insulating ceramic layer (192) of the heater substrate (190) is preferably designed to be lower than that of the ceramic layer (192) adjoining the external porous electrode (44) of the oxygen pump cell (40), and is importantly designed to be higher than that of the external porous electrode (44) so as to smoothly drain off the oxygen from the external electrode (44) via the porous ceramic layers (241, 243) and vent to outside the plural-cell gas sensor (3). The porosity of the thermal conductive porous ceramic layer (182, 183, 241, 243) may be preferably adjusted in the range of 20% to 80%, or more preferably of 30-70%, by varying a volume of porosity generators such as carbon particles, theobromine powder, organic fibers and a mixture thereof to be mixed in a green porous ceramic layer. The generators are burnt off during calcining or firing of the green porous ceramic layer in a process of co-firing a green laminate of the multi-cell layers and the heater substrate to leave pores.

The thermal conductive porous ceramic layer (241) adjoining the insulating ceramic layer (192) is preferably designed to contain more alumina than the thermal conductive porous ceramic layer (243) adjoining the external porous electrode (44) of the oxygen pump cell (40), when a mixture of alumina and zirconia is used in these plural porous ceramic layers (241, 243). Such an arrangement is preferred for transferring oxygen through the porous ceramic layers from the main internal space 210 and for avoiding possible crack formation in the porous ceramic layer (243) and the adjacent external electrode (44) during and/or after co-firing a green laminate of the multilayer cell gas sensors (3). For example, a mixture comprising about 40-60% by weight of alumina and about 40-60% by weight of zirconia is preferably used for the porous ceramic layer (243) adjoining the external porous electrode (44), and a mixture of about 60-100% by weight of alumina and about 0-40% by weight of zirconia is preferably used for the other porous ceramic layer (241).

When the thermal conductive porous ceramic layer (182, 183, 241, 243) contains zirconia, even in a case where current leaks from the heating resistor (60) to the external electrode of the pump cell (40) superimposed on the oxygen ion pumping current of the pump cell (40), the pump cell is not adversary affected, as compared to other cells such as the monitor cell and the gas detection cell having a comparatively very low ion current or signal on the order of microamperes, compared to that of the oxygen pump cell with an ion current flow on the order of milliamperes. This is another advantage of directly adjoining the thermal conductive porous layer (182) with the heater substrate (190) and the external electrode (44) of the oxygen pump cell (40), to be formed on the side of the oxygen pump cell incorporated in the multilayer plural-cell gas sensor.

In operation, oxygen inside the first main internal space (210) is pumped out through the first oxygen ion conductive solid electrolyte layer (170) and drained off from the external porous electrode (44) of the pump cell 40) via the porous ceramic layer (182) so as to vent to an ambient gas atmosphere outside the gas sensor (1). The gas having a reduced oxygen concentration in the main first internal space (210) and thereby made rich in a specific gaseous component concentration diffuses into the second and third internal spaces through the second inlet (216) so as to be analyzed by the gas detection cell (20) formed in the third internal space (230). When a specific gas component, for instance, NOx contacts the inner-detection electrode (22) of the gas detection cell (20), NOx dissociates into N and Ox that causes an ion current to flow across the inner detection electrode (22) and reference electrode (24) of the gas detection cell (20), thereby enabling measurement of NOx concentration based on the ion current. When a burnable gas component such as CO, HC, $NH_3$ contacts the detection electrode (22), the gas is burnt such that an EMF voltage or current across the detection cell (22) goes down or reverses, thereby enabling detection of such a burnable gas.

Figure 3:
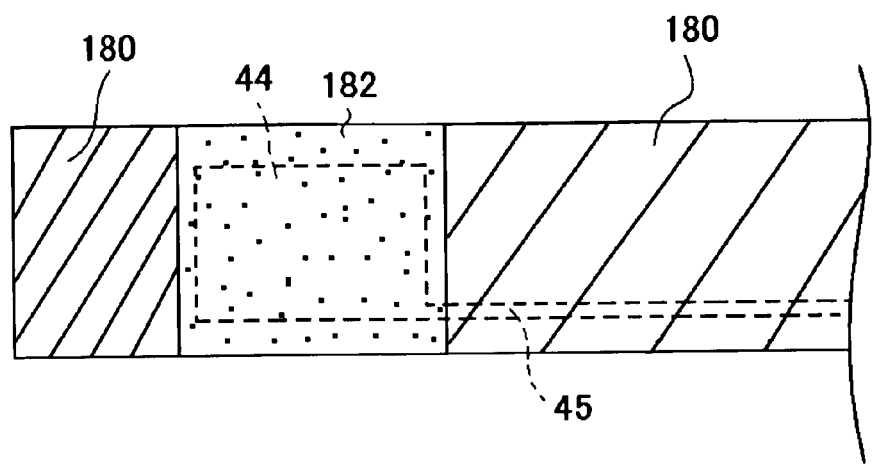
FIG. 3 is a schematic cross-sectional view, as cut along line A-A of FIG. 1, showing a porous ceramic layer (182) formed on an external electrode (44) of the oxygen pump cell (40) of FIG. 1.

In the plural-cell gas sensor (1) illustrated in FIGS. 1 and 2, or in the plural cell gas sensor (3) illustrated in FIG. 6, the thermal conductive porous ceramic layer (182, 241, 243) extends laterally and is exposed to the ambient gas atmosphere at two open windows formed in the longitudinal lateral sides of the plural-cell gas sensor (1, 3), as understood from FIGS. 1 and 3, via which the oxygen vents from inside of the gas sensor. In the plural-cell gas sensor (2) as illustrated in FIG. 4, the thermal conductive porous ceramic layer (183) is exposed to the ambient gas atmosphere at an open window formed at a front distal end of the plural cell gas sensor (2), as understood from FIGS. 4 and 5. Because fast venting of oxygen is lately required, a gas sensor having at least two windows formed at the laterals sides, the distal end and formed through the heater substrate (190) so as to expose a part of the thermal conductive porous ceramic layer to the ambient gas atmosphere is most preferable. From a viewpoint of mechanical and structural strength, a single window from which the oxygen vents to the external atmosphere is most preferable.

The multi-cell portion is preferably located at a distance of about 0.5-7 mm from the distal end of the longitudinally extending rod-like gas sensor, having a rectangular cross section. The length of the gas sensor is preferably designed to be about 35-75 mm. The width and the thickness thereof are preferably designed to be about 3-6 mm and 0.5 to 3.5 mm, respectively.

The total thickness of the thermal conductive solid electrolyte layer adjoining the external electrode (44) and the heater substrate (190) is preferably designed to be about 20-500 μm. The porous electrodes of the oxygen pump cell, the oxygen monitor cell and the gas detection cell, respectively have a thickness of about 5-50 μm. The oxygen pump cell, the oxygen monitor cell and the gas detection cell, respectively, preferably have a thickness of about 80-400 μm. The insulating ceramic layers (120, 160, 180, 192 and 194) are designed to have a thickness of about 200-300 μM, 30-250 μm, 20-500 μm, 80-500 μm and 80-500 μm, respectively. The first, second and third spaces (210, 220, 230) each has a spaced gap of about 30-250 μm measured across the layers forming the respective gaps. The respective area of the internal and external electrodes (42, 44) of the oxygen pump cell (40) is preferably 4-28 mm². The oxygen monitor cell electrodes (32, 34) and the gas detection cell electrodes (22, 24) are designed smaller in area than the pump cell electrodes (42, 44). These dimensional data are based on the plural cell gas sensor as fired.

This application is based on Japanese Patent Application No. 2005-193988 filed Jul. 1, 2005, incorporate herein by reference in its entirety.

What is claimed is:

1. A plural-cell gas sensor including:
    an oxygen pump cell comprising a first oxygen-ion conductive solid electrolyte ceramic layer and internal and external porous electrode layers sandwiching the first solid electrolyte ceramic layer;
    an oxygen monitor cell comprising a second oxygen-ion conductive solid electrolyte ceramic layer and inner and reference electrode layers sandwiching the second oxygen-ion conductive solid electrolyte ceramic layer;
    an internal space defined between the oxygen pump cell layer and the oxygen monitor cell;
    a gas-diffusion inlet through which a gas under measurement enters the internal space;
    a heater substrate comprising first and second insulating ceramic layers and a heating resistor embedded in the insulating ceramic layers; and
    a thermal conductive porous ceramic layer sandwiched by the oxygen pump cell and the heater substrate, the first insulating ceramic layer arranged closer to the thermal conductive porous ceramic layer than the second insulating ceramic layer;
    wherein the thermal conductive porous ceramic layer adjoins the external porous electrode of the oxygen pump cell and the insulating ceramic layer of the heater substrate such that oxygen inside the internal space is pumped out through the first oxygen ion conductive solid electrolyte layer and drained off from the external porous electrode of the pump cell layer via the porous ceramic layer so as to vent to an ambient gas atmosphere outside the gas sensor and such that heat from the heater substrate is directly transferred via the thermal conductive porous ceramic layer to the external electrode of the oxygen pump cell, and
    wherein the thermal conductive porous layer covers a part of the external porous electrode layer, the thermal conductive porous layer is only exposed at a lateral side of the plural-cell gas sensor, and having a longitudinally extended rod-like appearance.

2. The plural-cell gas sensor as claimed in claim 1, wherein the thermal conductive porous ceramic layer which adjoins the porous electrode layer of the oxygen pump cell and the insulating ceramic layer of the heater substrate is greater in porosity than the external porous electrode of the oxygen pump cell.

3. The plural-cell gas sensor as claimed in claim 1, wherein the thermal conductive porous ceramic layer has a porosity of 20% to 80%.

4. The plural-cell gas sensor as claimed in claim 1, wherein the porous ceramic layer mainly comprises alumina, zirconia, mullite, spinel or mixtures thereof.

5. The plural-cell gas sensor as claimed in claim 1, wherein the plural-cell gas sensor is a co-fired plural cell gas sensor made by co-firing a green laminate of layers constituting the oxygen pump cell, the heater substrate and the porous ceramic layer filled between the external electrode of the pump cell and the heater substrate.

6. The plural-cell gas sensor as claimed in claim 1, wherein the porous ceramic layer adjoining the external electrode of the oxygen pump cell and the heater substrate comprises plural porous ceramic layers adjoining one another, each layer differing from the other(s) in material composition or porosity.

7. The plural-cell gas sensor as claimed in claim 6, wherein a porous ceramic layer located closer to the external electrode of the oxygen pump cell contains more porous zirconia than a porous ceramic layer located closer to the heater substrate.

8. The plural-cell gas sensor as claimed in claim 6, wherein the porous ceramic layer located closest to the heater substrate has a porosity that is lower than that of the other porous ceramic layer(s).

9. The plural-cell gas sensor as claimed in claim 1, wherein the first and second oxygen-ion conductive solid electrolyte ceramic layers each comprises stabilized or partially stabilized zirconia and 10-80% by weight of alumina.

10. The plural-cell gas sensor as claimed in claim 5, wherein the first and second oxygen-ion conductive solid electrolyte ceramic layers each comprises stabilized or partially stabilized zirconia and 10-80% by weight of alumina.

11. The plural-cell gas sensor as claimed in claim 1, further including:
    a gas detection cell comprising a third oxygen-ion conductive solid electrolyte layer; and
    another internal space formed partly by the gas detection cell;
    wherein a gas reduced in concentration of oxygen and made rich in a specific gas component in the main internal space, by pumping action of the oxygen pump cell, compared to the gas under measurement entering the main internal space, enters the another internal space.

12. The plural-cell gas sensor as claimed in claim 11, wherein the specific gas component is NOx.

13. The-plural-cell gas sensor as claimed in claim 1, wherein the porous ceramic layer mainly comprises alumina.

14. The-plural-cell gas sensor as claimed in claim 1, wherein the porous ceramic layer mainly comprises zirconia.

15. The-plural-cell gas sensor as claimed in claim 1, wherein the porous ceramic layer mainly comprises mixtures of alumina and zirconia.

* * * * *